United States Patent
Yoshida et al.

(10) Patent No.: US 7,253,154 B2
(45) Date of Patent: Aug. 7, 2007

(54) SUBSTITUTED THIAZOLOPYRIMIDINES AS XANTHINE OXIDASE INHIBITORS

(75) Inventors: Shinichi Yoshida, Chiba (JP); Atsushi Tendo, Saitama (JP); Kunio Kobayashi, Saitama (JP); Nobutaka Mochiduki, Chiba (JP); Tomio Yamakawa, Chiba (JP); Yoriko Shinohara, Chiba (JP)

(73) Assignee: Nippon Chemiphar Co., Ltd., Tokyo (JP)

( * ) Notice: Subject to any disclaimer, the term of this patent is extended or adjusted under 35 U.S.C. 154(b) by 59 days.

(21) Appl. No.: 10/495,844

(22) PCT Filed: Nov. 14, 2002

(86) PCT No.: PCT/JP02/11893

§ 371 (c)(1),
(2), (4) Date: Oct. 22, 2004

(87) PCT Pub. No.: WO03/042185

PCT Pub. Date: May 22, 2003

(65) Prior Publication Data

US 2005/0090472 A1     Apr. 28, 2005

(30) Foreign Application Priority Data

Nov. 16, 2001  (JP)  .............................. 2001-352340

(51) Int. Cl.
| | |
|---|---|
| *C07D 487/04* | (2006.01) |
| *C07D 9/40* | (2006.01) |
| *A61K 31/519* | (2006.01) |
| *A61K 31/675* | (2006.01) |
| *A61P 19/06* | (2006.01) |
| *C07D 473/28* | (2006.01) |
| *C07D 473/34* | (2006.01) |
| *C07D 473/32* | (2006.01) |
| *C07D 473/30* | (2006.01) |
| *C07D 473/00* | (2006.01) |
| *C07D 471/04* | (2006.01) |
| *C07D 235/02* | (2006.01) |
| *C07D 277/66* | (2006.01) |
| *C07D 263/57* | (2006.01) |
| *A61K 31/522* | (2006.01) |
| *A61K 31/52* | (2006.01) |
| *A61K 31/423* | (2006.01) |
| *A61K 31/4184* | (2006.01) |
| *A61K 31/428* | (2006.01) |
| *A61K 31/4188* | (2006.01) |
| *A61K 31/424* | (2006.01) |
| *A61K 31/429* | (2006.01) |

(52) U.S. Cl. .................. 514/81; 514/260.1; 514/263.3; 514/263.4; 514/263.1; 514/301; 514/302; 514/303; 514/367; 514/375; 514/394; 544/255; 544/244; 544/276; 544/265; 544/264; 544/277; 546/21; 546/118; 546/114; 546/115; 548/112; 548/303.1; 548/153; 548/152; 548/218; 548/224

(58) Field of Classification Search ................ 544/255, 544/244; 514/260.1, 81
See application file for complete search history.

(56) References Cited

U.S. PATENT DOCUMENTS

| 4,038,396 A | 7/1977 | Shen et al. |
| 4,299,834 A | 11/1981 | Austel et al. |

FOREIGN PATENT DOCUMENTS

| GB | 2 119377 A | 4/1983 |
| JP | 03-258770 | 11/1991 |
| WO | WO 01/96299 A2 | 12/2001 |
| WO | WO 01/96336 A2 | 12/2001 |
| WO | WO 03/074516 A1 | 9/2003 |

*Primary Examiner*—Mark L. Berch
*Assistant Examiner*—Susanna Moore
(74) *Attorney, Agent, or Firm*—Reed Smth LLP

(57) ABSTRACT

The invention relates to compounds of the following formula (I) or their salts:

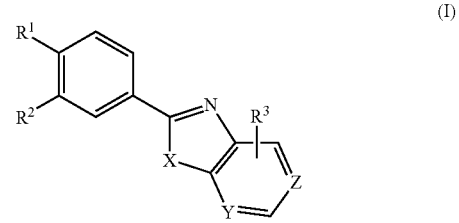

in which $R^1$ represents $OR^4$ or others, in which $R^4$ is an alkyl group having 1-8 carbon atoms which may have a substituent or the like; $R^2$ is halogen, nitro, cyano, carboxyl, or the like; $R^3$ is hydrogen, halogen, hydroxyl, amino, carboxyl, or the like; X is $NR^{11}$, oxygen, or sulfur, in which $R^{11}$ is hydrogen, or an alkyl group having 1-8 carbon atom which may have a substituent; and each of Y and Z is $CR^{12}$ or nitrogen, in which $R^{12}$ has the same meaning as $R^3$ above, and a xanthine oxidase inhibitor containing the compound as an active ingredient.

9 Claims, No Drawings

SUBSTITUTED THIAZOLOPYRIMIDINES AS XANTHINE OXIDASE INHIBITORS

CROSS-REFERENCES TO RELATED APPLICATIONS

This application is a National Phase application of PCT/JP02/11893 filed Nov. 14, 2002 which claims priority of Japanese Application No 2001-352340 filed on Nov. 16, 2001, the complete disclosure of which are hereby incorporated by reference.

FIELD OF THE INVENTION

The present invention relates to a xanthine oxidase inhibitor.

BACKGROUND OF THE INVENTION

The hyperuricemia causes gout and renal insufficiency and is also considered to be a factor causing coronary disease. Furthermore, the hyperuricemia is suggested to closely relate to the development of diseases of adults such as hypertension. Therefore, treatment of the hyperuricemia can be effective not only for treating gout but also for preventing various diseases relating to daily nutrition and the advancement of age.

Presently, the hyperuricemia is treated using an inhibitor for inhibiting production of uremic acid such as allopurinol and an accelerator for uricotelism such as benzbromalone. However, it is well known that allopurinol causes side effects such as lesion, hepatopathy, and myelogenetic troubles. The allopurinol and its metabolic product (oxypurinol) are excreted from the kidneys. However, if the excretion of uric acid decreases, the excretion of these compounds also decreases and the concentrations of these compounds in blood increase. Therefore, the chance of causing side effects increases.

It is reported that benzbromalone also causes hepatopathy. Accordingly, it is desired to develop new pharmaceuticals so that the practitioners can select more appropriate pharmaceuticals with less side effects.

Recently, the below-mentioned xanthine oxidase inhibitors having no purine nucleus such as TMX-67 (Teijin Corporation), Y-700 (Mitsubishi Wellpharma Corporation) and KT651 (Kotobuki Corporation) have been reported:

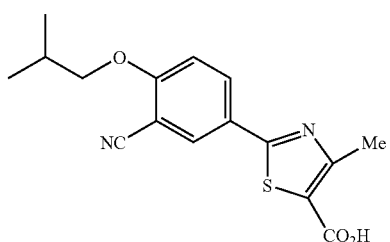

TMX-67

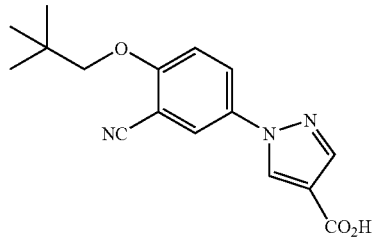

Y-700

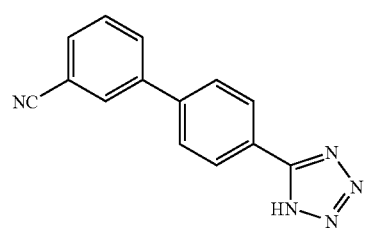

KT651

The present inventors have discovered that compounds of the below-mentioned formula (I) containing a bicyclic condensed hetero ring have a xanthine oxidase inhibiting effect. The present invention has been completed based on this discovery.

There are known, as compounds structurally analogous to the compounds of the invention, 2-phenylbenzazole compounds (in Japanese Patent Provisional Publication (Toku-15 hyo) 11-501024) and 2-phenylbenzimidazole compounds (in Japanese Patent Provisional Publication 56-5465). The former compounds have an amino group in the 4th position of the benzene ring and show an antitumor effect, while the latter compounds have 2-hydroxy-3-N-substituted aminopropoxy group in the 4th position of the benzene ring and show a hypotension inducing effect. Accordingly, these compounds differ from the compounds of the invention in their structures and pharmacological effects.

SUMMARY OF THE INVENTION

The present invention has an object: to provide compounds of the below-mentioned formula (I) which have a xanthine oxidase (XOD) inhibiting effect.

The invention resides in the compounds of the following formula (I) and their salts:

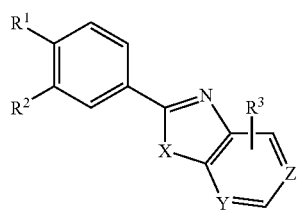

in which $R^1$ represents an alkyl group having 1-8 carbon atoms, an alkyl group substituted with 1-3 halogen atoms, $OR^4$, $CO_2R^5$, or $S(O)_nR^6$; wherein $R^4$ is hydrogen, or an alkyl group having 1-8 carbon atoms, an aralkyl group having an aryl moiety of 6-10 carbon atoms and an alkyl moiety of 1-4 carbon atoms, an alkylcarbonyl group having 2-9 carbon atoms, an arylcarbonyl group having an aryl moiety of 6-10 carbon atoms, an aralkylcarbonyl group having an aryl moiety of 6-10 carbon atoms and an alkylcarbonyl moiety of 2-5 carbon atoms or an aryl group having 6-10 carbon atoms which may have a substituent selected from the group consisting of halogen, hydroxyl, nitro and cyano; each of $R^5$ and $R^6$ is hydrogen or an alkyl group having 1-8 carbon atoms, an aralkyl group having an aryl moiety of 6-10 carbon atoms and an alkyl moiety of 1-4 carbon atoms, or an aryl group having 6-10-carbon atoms which may have substituent selected from the group consisting of halogen, hydroxyl, nitro, cyano and amino; and n is an integer of 0 to 2;

$R^2$ is hydrogen, halogen, nitro, cyano, formyl, an alkyl group having 1-8 carbon atoms, an alkyl group having 1-8 carbon atoms which is substituted with one to three halogens, or $CO_2R^7$ wherein $R^7$ has the same meaning as $R^5$ above;

$R^3$ is hydrogen, halogen, hydroxyl, amino, $CO_2R^8$, $PO_3H$, $PO(OH)(OR^9)$, $S(O)_mR^{10}$, or an alkyl group having 1-8 carbon atoms or an alkylaminocarbonyl group having alkyl of 1-8 carbon atoms which may have a substituent selected from the group consisting of halogen, hydroxyl, nitro, cyano and amino; wherein each of $R^8$, $R^9$, and $R^{10}$ has the same meaning as $R^5$ above; m has the same meaning as n above;

X is $NR^{11}$, oxygen, or sulfur, wherein $R^{11}$ is hydrogen, or an alkyl group having 1-8 carbon atom which may have a substituent selected from the group consisting of halogen, hydroxyl, nitro, cyano and amino; and each of Y and Z is $CR^{12}$ or nitrogen, wherein $R^{12}$ has the same meaning as $R^3$ above.

In addition, the invention relates to a xanthine oxidase inhibitor containing a compound of the formula (I) or a salt thereof as an active component.

DETAILED DESCRIPTION OF THE INVENTION

Furthermore, the invention relates to an agent for treating hyperuricemia containing a compound of the formula (I) or a salt thereof as an active component.

The invention is further described below in detail. Examples of the alkyl groups having 1-8 carbon atoms for $R^1$, $R^2$, $R^3$, $R^4$, $R^5$, $R^6$ and $R^{11}$ in the formula (I) include methyl, ethyl, propyl, isopropyl, butyl, isobutyl, t-butyl, and pentyl.

Examples of the alkyl groups having 1-8 carbon atoms for $R^1$ and $R^2$ include methyl, ethyl, propyl, isopropyl, butyl, isobutyl, t-butyl, and pentyl which are substituted with one to three fluorines, chlorines, or bromines. Examples of the aralkyl groups having an aryl moiety of 6-10 carbon atoms and an alkyl moiety of 1-4 carbon atoms for $R^4$, $R^5$ and $R^6$ include benzyl and phenethyl.

Examples of the alkylcarbonyl groups having 2-9 carbon atoms for $R^4$ include acetyl and propionyl.

Examples of the arylcarbonyl groups having an aryl moiety of 6-10 carbon atoms include benzoyl.

Examples of the aralkylcarbonyl groups having an aryl moiety of 6-10 carbon atoms and an alkylcarbonyl moiety of 2-5 carbon atoms include benzylcarbonyl.

Examples of the aryl groups having 6-10 carbon atoms for $R^4$, $R^5$ and $R^6$ include phenyl and naphthyl.

Examples of the halogen substituents for $R^2$, $R^3$, $R^4$, $R^5$, $R^6$, or $R^{11}$ include fluorine, chlorine, and bromine. Examples of the alkylaminocarbonyls having an alkyl moiety of 1-8 carbon atoms include methylaminocarbonyl.

(1) Preferred is a compound of the formula (I) in which $R^1$ is $OR^4$, and a salt thereof.

(2) Also preferred is a compound of the formula (I) in which $R^1$ is an alkoxy group having 1-5 carbon atoms, and a salt thereof.

(3) Also preferred is a compound of the formula (I) in which $R^1$ is isobutoxy and a salt thereof.

(4) Also preferred is a compound of the formula (I) in which $R^2$ is nitro, cyano, halogen, or carboxyl, and a salt thereof.

(5) Also preferred is a compound of the formula (I) or according to (1) to (3) above in which $R^3$ is nitro or cyano, and a salt thereof.

(6) Also preferred is a compound of the formula (I) or according to (1) to (5) above in which $R^3$ is hydrogen, amino, hydroxyl, halogen, or carboxyl, and a salt thereof.

(7) Also preferred is a compound of the formula (I) or according to (1) to (6) above in which X is NH or oxygen, and each of Y and Z is nitrogen, and a salt thereof.

(8) Also preferred is a compound of the formula (I) or according to (1) to (6) above in which X is sulfur, oxygen or NH, and Y is CH, C—OH or C—$CO_2H$, and Z is CH, and a salt thereof.

(9) Also preferred is a compound of the formula (I) or according to (1) to (6) above in which X is NH, and at least one of Y and Z is nitrogen and another is CH, and a salt thereof.

The compound of the formula (I) can be in the form of a pharmacologically acceptable salt. For instance, $R^5$, $R^7$, or $R^8$ is an alkali metal such as sodium, potassium, or lithium.

Processes for preparing a compound of the formula (I) are illustrated below.

[Synthesis Process 1—in the Case of X=NH or O]

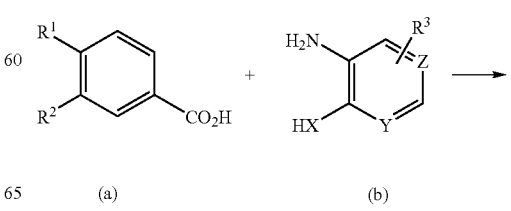

(a)           (b)

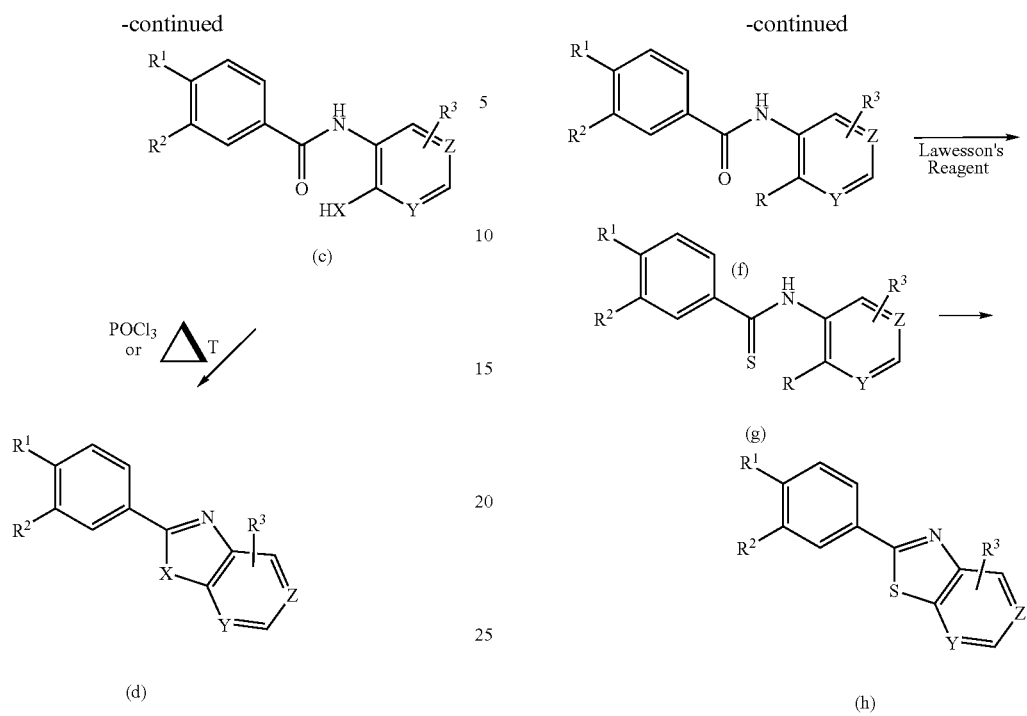

[in the formula, X is NH or O, and each of $R^1$, $R^2$, $R^3$, Y and Z has the same meaning as above.]

The benzamide derivative of the formula (c) can be obtained by reacting a benzoic acid derivative of the formula (a) with an aniline derivative of the formula (b).

The reaction can be carried out in the conventional manner for the formation of an amide compound. For instance, a benzoic acid derivative of the formula (a) is first converted into an acid chloride using thionyl chloride or oxalyl chloride, and then the acid chloride is reacted with an aniline derivative of the formula (b) in the presence of a solvent such as water or THF and in the presence or absence of, a base such as sodium hydrogen carbonate or triethylamine. Otherwise, a benzoic acid derivative of the formula (a) is reacted with an aniline derivative of the formula (b) in the presence of a condensing agent such as DDC or WSC—HCl.

The resulting benzoic amide of the formula (c) is reacted with phosphorus oxychloride or heated to give the compound of the invention represented by the formula (d).

[Synthesis Process 2—in the Case of: X=S]

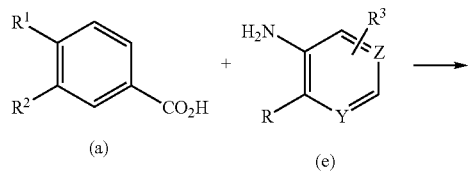

[in which R is hydrogen or halogen such as chlorine, and $R^1$, $R^2$, $R^3$, Y and Z are the same as those identified above.

The benzamide derivative of the formula (f) can be obtained by reacting a benzoic acid derivative of the formula (a) with an aniline derivative of the formula (e).

The amide forming reaction can be carried out in the same manner as described in the Synthesis process 1.

A benzoic thioamide derivative of the formula (g) can be prepared from a benzoic amide of the formula (f) by treatment with Lawesson's reagent.

The thiobenzamide derivative of the formula (g) is then treated with potassium ferricyanide and sodium hydride, to give a compound of the invention represented by the formula (h).

Other compounds represented by the formula (I) can be prepared in analogous manners.

Examples of the compounds of the invention are illustrated in the following tables 1 to 19.

(1) Examples of the following compounds having $NR^{11}$ for X are set forth in the following tables 1 to 7.

TABLE 1

| $R^1$ | $R^2$ | $R^3$ position 4- | $R^3$ position 6- | $R^{11}$ | Y | Z |
|---|---|---|---|---|---|---|
| O-isoBu | $NO_2$ | H | H | H | N | N |
| O-isoBu | $NO_2$ | Cl | H | H | N | N |
| O-isoBu | $CO_2H$ | Cl | H | H | N | N |

TABLE 1-continued

Structure: 2-(aryl)imidazo-fused bicyclic with substituents R¹, R², R³ (positions 4, 6), R¹¹, Y, Z.

| R¹ | R² | 4- | 6- | R¹¹ | Y | Z |
|---|---|---|---|---|---|---|
| O-isoBu | Cl | Cl | H | H | N | N |
| O-isoBu | NO₂ | Cl | H | Me | N | N |
| O-isoBu | NO₂ | H | Cl | H | N | N |
| O-isoBu | CN | Cl | H | H | N | N |
| O-isoPr | CN | Cl | H | H | N | N |
| O-isoBu | NO₂ | OH | H | H | N | N |
| O-isoBu | CO₂H | OH | H | H | N | N |
| O-isoBu | CHO | OH | H | H | N | N |
| O-isoBu | NO₂ | OH | H | Me | N | N |
| O-isoPr | NO₂ | H | OH | H | N | N |
| O-isoBu | CN | OH | H | H | N | N |

TABLE 2

| R¹ | R² | 4- | 6- | R¹¹ | Y | Z |
|---|---|---|---|---|---|---|
| O-isoPr | CN | OH | H | H | N | N |
| O-isoBu | NO₂ | NH₂ | H | H | N | N |
| O-isoBu | CO₂H | NH₂ | H | H | N | N |
| O-isoBu | CF₃ | NH₂ | H | H | N | N |
| O-isoBu | CHO | NH₂ | H | H | N | N |
| O-isoBu | NO₂ | NH₂ | H | Me | N | N |
| O-isoPr | NO₂ | H | NH₂ | H | N | N |
| O—Et | NO₂ | NH₂ | H | H | N | N |
| O—Me | NO₂ | NH₂ | H | H | N | N |
| CF₃ | NO₂ | NH₂ | H | H | N | N |
| IsoPr | NO₂ | NH₂ | H | H | N | N |
| OCH₂CO₂Et | NO₂ | NH₂ | H | H | N | N |
| O-isoBu | CN | NH₂ | H | H | N | N |
| O-isoPr | CN | H | NH₂ | H | N | N |

TABLE 3

| R¹ | R² | 4- | 6- | R¹¹ | Y | Z |
|---|---|---|---|---|---|---|
| O—Et | CN | NH₂ | H | H | N | N |
| O—Me | CN | NH₂ | H | H | N | N |
| CF₃ | CN | NH₂ | H | H | N | N |
| IPr | CN | NH₂ | H | H | N | N |
| OCH₂CO₂ | CN | NH₂ | H | H | N | N |
| O-isoBu | NO₂ | H | H | H | N | CH |
| O-isoBu | CO₂H | H | H | H | N | CH |
| O-isoBu | F | H | H | H | N | CH |
| O-isoBu | NO₂ | H | H | Me | N | CH |
| O-isoPr | NO₂ | H | H | H | N | CH |
| O-isoBu | CN | H | H | H | N | CH |
| O-isoPr | CN | H | H | H | N | CH |
| O-isoBu | NO₂ | H | H | H | N | COH |
| O-isoBu | NO₂ | H | H | H | N | CNH₂ |

TABLE 4

| R¹ | R² | 4- | 6- | R¹¹ | Y | Z |
|---|---|---|---|---|---|---|
| O-isoBu | NO₂ | H | H | H | N | CCO₂H |
| O-isoBu | NO₂ | H | H | H | CH | N |
| O-isoBu | CO₂H | H | H | H | CH | N |
| O-isoBu | CF₃ | H | H | H | CH | N |
| O-isoBu | NO₂ | H | H | Me | CH | N |
| O-isoPr | NO₂ | H | H | H | CH | N |
| O-isoBu | CN | H | H | H | CH | N |
| O-isoPr | CN | H | H | H | CH | N |
| O-isoBu | NO₂ | H | H | H | CH | CH |
| O-isoBu | CO₂H | H | H | H | CH | CH |
| O-isoBu | Cl | H | H | H | CH | CH |
| O-isoBu | NO₂ | H | H | Me | CH | CH |
| O-isoPr | NO₂ | H | H | H | CH | CH |
| O-isoBu | CN | H | H | H | CH | CH |

TABLE 5

| R¹ | R² | 4- | 6- | R¹¹ | Y | Z |
|---|---|---|---|---|---|---|
| O-isoPr | CN | H | H | H | CH | CH |
| O-isoBu | NO₂ | OH | H | H | CH | CH |
| O-isoBu | CO₂H | OH | H | H | CH | CH |
| O-isoBu | CHO | OH | H | H | CH | CH |
| O-isoBu | NO₂ | OH | H | Me | CH | CH |
| O-isoPr | NO₂ | H | OH | H | CH | CH |
| O-isoBu | CH | OH | H | H | CH | CH |
| O-isoBu | NO₂ | H | H | H | CH | COH |
| O-isoBu | NO₂ | H | H | H | H | CNH₂ |
| O-isoBu | NO₂ | H | H | H | CH | CCO₂H |
| O-isoBu | NO₂ | H | H | H | COH | N |
| O-isoBu | NO₂ | H | H | H | COH | CH |
| O-isoBu | CN | H | H | H | COH | CH |
| O-isoBu | CO₂H | H | H | H | COH | CH |

TABLE 6

| R¹ | R² | 4- | 6- | R¹¹ | Y | Z |
|---|---|---|---|---|---|---|
| O-isoBu | NO₂ | H | H | H | CNH₂ | N |
| O-isoBu | NO₂ | H | H | H | CNH₂ | CH |
| O-isoBu | NO₂ | H | H | H | CCO₂Me | N |
| O-isoBu | NO₂ | H | H | H | CCO₂ME | CH |
| O-isoBu | NO₂ | H | H | H | CCO₂H | N |
| O-isoBu | NO₂ | H | H | H | CCO₂H | CH |
| O-isoBu | CO₂H | H | H | H | CCO₂H | CH |
| O-isoBu | F | H | H | H | CCO₂H | CH |
| O-isoBu | CHO | H | H | H | CCO₂H | CH |
| O-isoBu | NO₂ | H | H | Me | CCO₂H | CH |
| O-isoPr | NO₂ | H | H | H | CCO₂H | XH |
| O—Et | NO₂ | H | H | H | CCO₂H | CH |
| O—Me | NO₂ | H | H | H | CCO2H | CH |
| CF3 | NO₂ | H | H | H | CCO₂H | CH |

TABLE 7

| R¹ | R² | R³ Position 4- | 6- | R¹¹ | Y | Z |
|---|---|---|---|---|---|---|
| isoPr | NO₂ | H | H | H | CCO₂H | CH |
| OCH₂CO₂Et | NO₂ | H | H | H | CCO₂H | CH |
| O-isoBu | CN | H | H | H | CCO₂H | CH |
| O-isoBu | CO₂H | H | H | H | CCO₂H | CH |
| O-isoBu | Cl | H | H | H | CCO₂H | CH |
| O-isoBu | CF₃ | H | H | Me | CCO₂H | CH |
| O-isoPr | CN | H | H | H | CCO₂H | CH |
| O—Et | CN | H | H | H | CCO₂H | CH |
| CF₃ | CN | H | H | H | CCO₂H | CH |
| IsoPr | CN | H | H | H | CCO₂H | CH |
| OCH₂CO₂Et | CN | H | H | H | CCO₂H | CH |
| O-isoBu | NO₂ | H | H | H | CPO₃H | N |
| O-isoBu | NO₂ | H | H | H | CPO₃H | CH |
| O-isoBu | NO₂ | H | H | H | CCONHMe | N |
| O-isoBu | NO₂ | H | H | H | CCONHMe | CH |

(2) Examples of the following compounds having 0 for X are set forth in the following tables 8 to 13.

TABLE 8

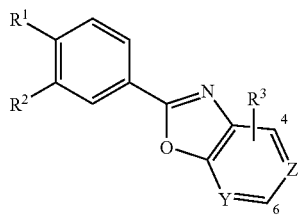

| R¹ | R² | R³ Position 4- | 6- | Y | Z |
|---|---|---|---|---|---|
| O-isoBu | NO₂ | H | H | N | N |
| O-isoBu | NO₂ | Cl | H | N | N |
| O-isoBu | Cl | Cl | H | N | N |
| O-isoPr | NO₂ | Cl | H | N | N |
| O-isoBu | CN | Cl | H | N | N |
| O-isoPr | CN | Cl | H | N | N |
| O-isoBu | NO₂ | OH | H | N | N |
| O-isoBu | CHO | OH | H | N | N |
| O-isoPr | NO₂ | OH | H | N | N |
| O-isoBu | CN | OH | H | N | N |
| O-isoPr | CN | OH | H | N | N |
| O-isoBu | NO₂ | NH₂ | H | N | N |
| O-isoBu | CO₂H | NH₂ | H | N | N |
| O-isoBu | CF₃ | NH₂ | H | N | N |

TABLE 9

| R¹ | R² | R³ Position 4- | 6- | Y | Z |
|---|---|---|---|---|---|
| O-isoBu | CHO | NH₂ | H | N | N |
| O-isoPr | NO₂ | H | NH₂ | N | N |
| O—Et | NO₂ | NH₂ | H | N | N |
| O—Me | NO₂ | NH₂ | H | N | N |
| CF₃ | NO₂ | NH₂ | H | N | N |
| IsoPr | NO₂ | NH₂ | H | N | N |
| OCH₂CO₂Et | NO₂ | NH₂ | H | N | N |
| O-isoBu | CN | NH₂ | H | N | N |
| O-isoPr | CN | H | NH₂ | N | N |
| O—Et | CN | NH₂ | H | N | N |

TABLE 9-continued

| R¹ | R² | R³ Position 4- | 6- | Y | Z |
|---|---|---|---|---|---|
| O—Me | CN | NH₂ | H | N | N |
| CF₃ | CN | NH₂ | H | N | N |
| IsoPr | CN | NH₂ | H | N | N |
| OCH₂CO₂Et | CN | NH₂ | H | N | N |

TABLE 10

| R¹ | R² | R³ Position 4- | 6- | Y | Z |
|---|---|---|---|---|---|
| O-isoBu | NO₂ | H | H | N | CH |
| O-isoBu | F | H | H | N | CH |
| O-isoPr | NO₂ | H | H | N | CH |
| O-isoBu | CN | H | H | N | CH |
| O-isoPr | CN | H | H | N | CH |
| O-isoBu | NO₂ | H | H | N | COH |
| O-isoBu | NO₂ | H | H | N | CNH₂ |
| O-isoBu | NO₂ | H | H | N | CCO₂H |
| O-isoBu | NO₂ | H | H | CH | N |
| O-isoBu | CF₃ | H | H | CH | N |
| O-isoPr | NO₂ | H | H | CH | N |
| O-isoBu | CN | H | H | CH | N |
| O-isoPr | CN | H | H | CH | N |
| O-isoBu | NO₂ | H | H | CH | CH |

TABLE 11

| R¹ | R² | R³ Position 4- | 6- | Y | Z |
|---|---|---|---|---|---|
| O-isoBu | Cl | H | H | CH | CH |
| O-isoPr | NO₂ | H | H | CH | CH |
| O-isoBu | CN | H | H | CH | CH |
| O-isoPr | CN | H | H | CH | CH |
| O-isoBu | NO₂ | OH | H | CH | CH |
| O-isoBu | CO₂H | OH | H | CH | CH |
| O-isoBu | COH | OH | H | CH | CH |
| O-isoPr | NO₂ | H | OH | CH | CH |
| O-isoBu | CN | OH | H | CH | CH |
| O-isoBu | NO₂ | H | H | CH | COH |
| O-isoBu | NO₂ | H | H | CH | CNH₂ |
| O-isoBu | NO₂ | H | H | CH | CCO₂H |
| O-isoBu | NO₂ | H | H | COH | N |
| O-isoBu | NO₂ | H | H | COH | CH |

TABLE 12

| R¹ | R² | R³ Position 4- | 6- | Y | Z |
|---|---|---|---|---|---|
| O-isoBu | CN | H | H | COH | CH |
| O-isoBu | NO₂ | H | H | CNH₂ | N |
| O-isoBu | NO₂ | H | H | CNH₂ | CH |
| O-isoBu | NO₂ | H | H | CCO₂Me | N |
| O-isoBu | NO₂ | H | H | CCO₂Me | CH |
| O-isoBu | NO₂ | H | H | CCO₂H | N |
| O-isoBu | NO₂ | H | H | CCO₂H | CH |
| O-isoBu | CO₂H | H | H | CCO₂H | CH |
| O-isoBu | F | H | H | CCO₂H | CH |
| O-isoBu | CHO | H | H | CCO₂H | CH |
| O-isoPr | NO₂ | H | H | CCO₂H | CH |

TABLE 12-continued

| R¹ | R² | R³ Position 4- | 6- | Y | Z |
|---|---|---|---|---|---|
| O—Et | NO₂ | H | H | CCO₂H | CH |
| O—Me | NO₂ | H | H | CCO₂H | CH |
| CF₃ | NO₂ | H | H | CCO₂H | CH |

TABLE 13

| R¹ | R² | R³ Position 4- | 6- | Y | Z |
|---|---|---|---|---|---|
| IsoPr | NO₂ | H | H | CCO₂H | CH |
| OCH₂CO₂Et | NO₂ | H | H | CCO₂H | CH |
| O-isoBu | CN | H | H | CCO₂H | CH |
| O-isoBu | CN | H | H | CCO₂H | CH |
| O-isoBu | Cl | H | H | CCO₂H | CH |
| O-isoPr | CN | H | H | CCO₂H | CH |
| O—Et | CN | H | H | CCO₂H | CH |
| CF₃ | CN | H | H | CCO₂H | CH |
| IsoPr | CN | H | H | CCO₂H | CH |
| OCH₂CO₂Et | CN | H | H | CCO₂H | CH |
| O-isoBu | NO₂ | H | H | CPO₃H | N |
| O-isoBu | NO₂ | H | H | CPO₃H | CH |
| O-isoBu | NO₂ | H | H | CCONHMe | N |
| O-isoBu | NO₂ | H | H | CCONHMe | CH |

(3) Examples of the following compounds having S for X are set forth in the following tables 14 to 19.

TABLE 14

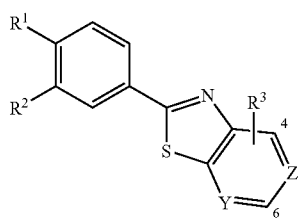

| R¹ | R² | R³ Position 4- | 6- | Y | Z |
|---|---|---|---|---|---|
| O-isoBu | NO₂ | H | H | N | N |
| O-isoBu | NO₂ | Cl | H | N | N |
| O-isoBu | Cl | Cl | H | N | N |
| O-isoPr | NO₂ | Cl | H | N | N |
| O-isoBu | CN | Cl | H | N | N |
| O-isoPr | CN | Cl | H | N | N |
| O-isoBu | NO₂ | OH | H | N | N |
| O-isoBu | CHO | OH | H | N | N |
| O-isoPr | NO₂ | OH | H | N | N |
| O-isoBu | CN | OH | H | N | N |
| O-isoPr | CN | OH | H | N | N |
| O-isoBu | NO₂ | NH₂ | H | N | N |
| O-isoBu | CO₂H | NH₂ | H | N | N |
| O-isoBu | CF₃ | NH₂ | H | N | N |

TABLE 15

| R¹ | R² | R³ Position 4- | 6- | Y | Z |
|---|---|---|---|---|---|
| O-isoBu | CHO | NH₂ | H | N | N |
| O-isoPr | NO₂ | H | NH₂ | N | N |
| O—Et | NO₂ | NH₂ | H | N | N |
| O—Me | NO₂ | NH₂ | H | N | N |
| CF₃ | NO₂ | NH₂ | H | N | N |
| isoPr | NO₂ | NH₂ | H | N | N |
| OCH2CO₂Et | NO₂ | NH₂ | H | N | N |
| O-isoBu | CN | NH₂ | H | N | N |
| O-isoPr | CN | H | NH₂ | N | N |
| O—Et | CN | NH₂ | H | N | N |
| O—Me | CN | NH₂ | H | N | N |
| CF₃ | CN | NH₂ | H | N | N |
| isoPr | CN | NH₂ | H | N | N |
| OCH₂CO₂Et | CN | NH₂ | H | N | N |

TABLE 16

| R¹ | R² | R³ Position 4- | 6- | Y | Z |
|---|---|---|---|---|---|
| O-isoBu | NO₂ | H | H | N | CH |
| O-isoBu | F | H | H | N | CH |
| O-isoPr | NO₂ | H | H | N | CH |
| O-isoBu | CN | H | H | N | CH |
| O-isoPr | CN | H | H | N | CH |
| O-isoBu | NO₂ | H | H | N | COH |
| O-isoBu | NO₂ | H | H | N | CNH₂ |
| O-isoBu | NO₂ | H | H | N | CCO₂H |
| O-isoBu | NO₂ | H | H | CH | N |
| O-isoBu | CF₃ | H | H | CH | N |
| O-isoPr | NO₂ | H | H | CH | N |
| O-isoBu | CN | H | H | CH | N |
| O-isoPr | CN | H | H | CH | N |
| O-isoBu | NO₂ | H | H | CH | CH |

TABLE 17

| R¹ | R² | R³ Position 4- | 6- | Y | Z |
|---|---|---|---|---|---|
| O-isoBu | Cl | H | H | CH | CH |
| O-isoPr | NO₂ | H | H | CH | CH |
| O-isoBu | CN | H | H | CH | CH |
| O-isoPr | CN | H | H | CH | CH |
| O-isoBu | NO₂ | OH | H | CH | CH |
| O-isoBu | CO₂H | OH | H | CH | CH |
| O-isoBu | CHO | OH | H | CH | CH |
| O-isoPr | NO₂ | H | OH | CH | CH |
| O-isoBu | CN | OH | H | CH | CH |
| O-isoBu | NO₂ | H | H | CH | COH |
| O-isoBu | NO₂ | H | H | CH | CNH₂ |
| O-isoBu | NO₂ | H | H | CH | CCO₂H |
| O-isoBu | NO₂ | H | H | COH | N |
| O-isoBu | NO₂ | H | H | COH | CH |

TABLE 18

| R$^1$ | R$^2$ | R$^3$ Position 4- | 6- | Y | Z |
|---|---|---|---|---|---|
| O-isoBu | CN | H | H | COH | CH |
| O-isoBu | NO$_2$ | H | H | CNH$_2$ | N |
| O-isoBu | NO$_2$ | H | H | CNH$_2$ | CH |
| O-isoBu | NO$_2$ | H | H | CCO$_2$Me | N |
| O-isoBu | NO$_2$ | H | H | CCO$_2$Me | CH |
| O-isoBu | NO$_2$ | H | H | CCO$_2$H | N |
| O-isoBu | NO$_2$ | H | H | CCO$_2$H | CH |
| O-isoBu | CO$_2$H | H | H | CCO$_2$H | CH |
| O-isoBu | F | H | H | CCO$_2$H | CH |
| O-isoBu | CHO | H | H | CCO$_2$H | CH |
| O-isoPr | NO$_2$ | H | H | CCO$_2$H | CH |
| O—Et | NO$_2$ | H | H | CCO$_2$H | CH |
| O—Me | NO$_2$ | H | H | CCO$_2$H | CH |
| CF$_3$ | NO$_2$ | H | H | CCO$_2$H | CH |

TABLE 19

| R$^1$ | R$^2$ | R$^3$ Position 4- | 6- | Y | Z |
|---|---|---|---|---|---|
| IsoPr | NO$_2$ | H | H | CCO$_2$H | CH |
| OCH$_2$CO$_2$Et | NO$_2$ | H | H | CCO$_2$H | CH |
| O-isoBu | CN | H | H | CCO$_2$H | CH |
| O-isoBu | CN | H | H | CCO$_2$H | CH |
| O-isoBu | Cl | H | H | CCO$_2$H | CH |
| O-isoPr | CN | H | H | CCO$_2$H | CH |
| O—Et | CN | H | H | CCO$_2$H | CH |
| CF$_3$ | CN | H | H | CCO$_2$H | CH |
| IsoPr | CN | H | H | CCO$_2$H | CH |
| OCH$_2$CO$_2$Et | CN | H | H | CCO$_2$H | CH |
| O-isoBu | NO$_2$ | H | H | CPO$_3$H | N |
| O-isoBu | NO$_2$ | H | H | CPO$_3$H | CH |
| O-isoBu | NO$_2$ | H | H | CCONHMe | N |
| O-isoBu | NO$_2$ | H | H | CCONHMe | CH |

The pharmacological actions of the present invention are described below.

The xanthine oxidase inhibiting action (in vitro test) of the compound of the invention was confirmed by measuring inhibition of oxidation of xanthine by xanthine oxidase, as described in Example 13. As is clear from Table 20, the compounds of the invention show excellent xanthine oxidase inhibiting action.

The xanthine oxidase inhibiting action was further confirmed in vivo tests by measuring the uric acid concentration in a plasma obtained from mouse into which the compound of the invention had been orally administered. See Example 1-B, Table 21.

Accordingly, it is expected that the compounds of the invention having the formula (I) are employable for preventing or treating hyperuricemia and gout.

The compound of the invention can be administered into human beings by appropriate administration methods such as oral administration and parenteral administration.

The compounds of the invention can be prepared in the form of known pharmaceutical preparations such as pellets, granules, powders, capsules, suspensions, injections, and suppositories. For the preparations, a conventionally employed excipients, disintegrators, binder, lubricants, dyes, diluents, or the like are employed. The excipient may be lactose, D-mannitol, crystalline cellulose, or glucose. The disintegrator may be starch or carboxymethylcellulose calcium (CMC—Ca). The lubricant may be magnesium stearate or talc. The binder may be hydroxypropylcellulose (HPC), gelatin, or polyvinylpyrrolidone (PVP).

Generally, the adult dosage of the compound of the invention is approximately 0.1 to 100 mg/day when it is administered in the form of an injection, and approximately 1 to 2,000 mg/day when it is orally administered. The dosage can be adjusted depending on age and clinical conditions.

The present invention is further described below by the following non-limiting examples.

EXAMPLE 1

8-(4-Isobutoxy-3-nitrophenyl)-6-chloropurine (A) and 6-amino-8-(4-isobutoxy-3-nitrophenyl)15 oxazolo[4,5-d]pyrimidine (B)

(1) Methyl 4-hydroxy-3-nitrobenzoate

4-Hydroxy-3-nitrobenzoic acid (10.0 g, 54.6 mmol) was suspended in methanol (60 mL). After addition of conc. sulfuric acid (0.1 mL), the suspension was heated overnight under reflux. The methanol was distilled off under reduced pressure. The residue was dissolved in ethyl acetate (40 mL), washed successively with aqueous sodium hydrogen carbonate (20 mL×2) and saturated aqueous brine (20 mL), and dried over anhydrous sodium sulfate. The solvent was distilled off under reduced pressure, to give 6.27 g (yield 58%) of the desired compound in the form of a pale brown crystalline product.

M. p. 72-73° C. $^1$H NMR (CDCl$_3$, 400 MHz) δ: 3.95 (3H, s), 7.22 (1H, d, J=9 Hz), 8.24 (1H, dd, J=2 Hz, 9 Hz), 8.83 (1H, d, J=2 Hz), 10.89 (1H, s).

(2) Methyl 4-isobutyloxy-3-nitrobenzoate

Isobutyl bromide (10.5 mL, 95.8 mmol) was added to a suspension of methyl 4-hydroxy-3-nitrobenzoate (6.26 g, 31.8 mmol) and potassium carbonate (13.2 g, 95.5 mmol) in dry DMF (40 mL). The resulting mixture was stirred at 90° C. for 44 hours and then cooled to room temperature. Subsequently, ice-water (80 mL) was added to the cooled mixture. The precipitated crystalline product was collected by filtration, washed with water (50 mL), and dried for 30 min in air. The dried crystalline product was then washed with hexane (40 mL), and dried in air to give 7.03 g (yield 87%) of the desired compound in the form of a pale orange crystalline product.

M.p.: 77-77° C. $^1$H NMR (CDCl$_3$, 400 MHz) δ: 1.07 (6H, d, J=7 Hz), 2.1-2.3 (1H, m), 3.93 (2H, d, J=7 Hz), 3.93 (3H, s), 7.09 (1H, 20 d, J=9 Hz), 8.18 (1H, dd, J=2 Hz, 9 Hz), 8.50 (1H, d, J=2 Hz).

(3) 4-Isobutyloxy-3-nitrobenzoic acid

Methyl 4-isobutyloxy-3-nitrobenzoate (2.50 g, 9.87 mmol) was dissolved in a mixture of methanol (10 mL) and 25 THF (10 mL). After addition of 2M aqueous sodium hydroxide (7.5 mL, 15.0 mmol), the solution was stirred for 18 hours at room temperature. The solvent was distilled off under reduced pressure, and were added to the residue water (20 mL) and 3M aqueous hydrochloric acid to adjust 30 the solution to pH 1. The precipitated crystalline product was collected by filtration. The crystalline product was washed with water (20 mL×2) and dried at 50° C. for 4 hours under reduced pressure, to give 2.31 g (yield 98%) of the desired compound in the form of a white crystalline product.

M.p.: 184-186° C. $^1$H NMR (CDCl$_3$, 400 MHz) δ: 1.08 (6H, d, J=6 Hz), 2.12.3 (1H, m), 3.95 (2H, d, J=6 Hz), 7.13 (1H, d, J=9 Hz), 8.24 (1H, dd, J=2 Hz, 9 Hz), 8.56 (1H, d, J=2 Hz).

(4) 4-Amino-6-hydroxy-5-(4-isobutoxy-3-nitrobenzoyl)aminopyridine 4,5-Diamino-6-hydroxypyrimidine (527 mg, 4.18 mmol) was added to an aqueous suspension of sodium hydrogen carbonate (3.15 g, 41.8 mmol) in water (10 mL) under cooling with ice. Subsequently, a solution of 4-isobutoxy-3-nitrobenzoyl chloride (1.08 g, 4.18 mmol) in ethyl acetate (10 mL) was added. The resulting mixture was stirred for 3 hours under cooling with ice, made acetic by addition of 6 M hydrochloric acid, placed under reduced pressure at room temperature to distill ethyl acetate off, and stirred for 30 min. at room temperature. The precipitated solid product was collected by filtration, washed successively with water and diethyl ether, and dried successively in air and reduced pressure, to give 963 mg (yield 69%) of the desired compound in the form of a powdery product.

$^1$H NMR(DMSO-d$_6$, 400 MHz) δ: 1.00 (6H, d, J=6 Hz), 2.0-2.1 (1H, m), 4.03 (2H, d, J=6 Hz), 6.37 (2H, broad, s), 7.45 (1H, d, J=9 Hz), 7.78 (1H, s), 8.22 (1H, dd, J=2 Hz, 9 Hz), 8.44 (1H, d, J=2 Hz), 9.18 (1H, s), 11.70 (1H, s).

(5) 8-(4-Isobutoxy-3-nitrophenyl)-6-chloropurine (A) and 6-amino-8-(4-isobutoxy-3-nitrophenyl)oxazolo[4,5-d]pyrimidine (B)

A mixture of 4-amino-6-hydroxy-5-(4-isobutoxy-3nitrobenzoyl)aminopyridine (354 mg, 1.07 mmol) and phosphorus oxychloride (6 mL) was stirred at. 120° C. for 4.5 hours. Excessive phosphorus oxychloride was distilled off under reduced pressure. The residue was stirred for 30 min., after addition of ice-water. The insolubles (1) were removed by filtration and the filtrate was stirred for 30 min., after addition of aqueous 0.5 M sodium hydroxide (24 mL). The insolubles were then removed by filtration, and the aqueous portion was made acidic by addition of acetic acid. The precipitated solid product was collected by filtration. The collected solid product and the insolubles (2) were combined and subjected to silica gel column chromatography and eluted using ethyl acetate/n-hexane (2/1) to give 45 mg (yield 13%) of the desired compound (A) and 60 mg (yield 17%) of the desired compound (B), both in the form of a pale yellow powdery product.

(A) $^1$H NMR (CDCl$_3$-CD$_3$OD, 400 MHz) δ: 1.10 (6H, d, 25 J=7 Hz), 2.2-2.3 (1H, m), 3.98 (2H, d, J=7 Hz), 7.23 (1H, d, J=9 Hz), 8.48 (1H, dd, J=2 Hz, 9 Hz), 8.64 (1H, d, J=2 Hz), 8.74 (1H, s).

(B) 1H NMR (DMSO-d6, 400 MHz) δ: 1.01 (6H, d, J=7 Hz), 2.1-2.2 (1H, m), 4.07 (2H, d, J=7 Hz), 7.60 (1H, d, J=9 Hz), 7.77 (2H, broad, s), 8.25 (1H, s), 8.32 (1H, dd, J=2 Hz, 9 Hz), 8.55 (1H, d, J=2 Hz). FAB-MS (m/e): 330 (M+1).

EXAMPLE 2

8-(4-Isobutoxy-3-nitrophenyl)-6-hydroxypurine

A suspension of 8-(4-isobutoxy-3-nitrophenyl)-6chloropurine (30 mg, 0.086 mmol) in aqueous 2M hydrochloric acid (4.5 mL) was heated to 120° C. for 3 hours under stirring. The suspension was then cooled to room temperature. The precipitated solid product was collected by filtration, washed with water, and dried in air. The dried product was heated to 100° C. after addition of aqueous 2M hydrochloric acid (27 mL). The insolubles were removed while the aqueous portion was still hot. The filtrate was stirred overnight. The precipitated solid product was collected by filtration, washed with water, and dried in air, to give 12 mg (yield 43%) of the desired compound in the form of a yellow powdery product.

$^1$H NMR (DMSO-d$_6$, 400 MHz) δ: 1.00 (6H, d, J=7 Hz), 2.0-2.2 (1H, m), 4.03 (2H, d, J=6 Hz), 7.55 (1H, d, J=9 Hz), 8.02 (1H, s), 8.39 (1H, dd, J=2 Hz, 9 Hz), 8.65 (1H, J=2 Hz), 12.28 (1H, s). FAB-MS (m/e): 330 (M+1).

EXAMPLE 3

8-(4-Isobutoxy-3-nitrophenyl)-1H-benzimidazole 1,2-Phenylenediamine (1.09 g, 10.1 mmol) was dissolved in THF (20 mL). The solution was cooled with ice water, and to the cooled solution was dropwise added to a solution of 4-isobutoxy-3-nitrobenzoyl chloride (1.00 mmol) in THF (3 mL) for more than 30 min. The mixture was then stirred for 3 hours under cooling with ice-water. The solvent was distilled off under reduced pressure. The residue was suspended in water (20 mL) and stirred for 30 min., at room temperature. The obtained crystalline product was collected by filtration, washed with water (5 mL×3), and dried at room temperature under reduced pressure, to give 291 mg (yield 88%) of the desired amide product in the form of a pale yellow crystalline product.

The amide product (165 mg, 0.50 mmol) and phosphoryl chloride (3.0 mL) were together heated under reflux for 3 hours, and then allowed to stand and cooled to room temperature. The reaction mixture was poured into ice-water (50 mL), and the aqueous mixture was stirred for 30 min. The obtained crystalline product was collected by filtration, washed with water (5 mL×5), and dried at room temperature under reduced pressure, to give 142 mg (yield 91%) of the desired compound in the form of a pale yellow crystalline product.

M.p.: 235-240° C. (decomp.) $^1$H NMR (DMSO-d$_6$, 400 MHz) δ: 1.02 (6H, d, J=6 Hz), 2.0-2.2 (1H, m), 4.07 (2H, d, J=6 Hz), 7.3-7.4 (2H, m), 7.63 (1H, d, J=9 Hz), 7.7-7.8 (2H, m), 8.50 (1H, dd, 25 J=2 Hz, 9 Hz), 8.75 (1H, d, J=2 Hz).

EXAMPLE 4

2-(4-Isobutoxy-3-nitrophenyl)imidazolo[4,5b]pyridine (1) 2-Amino-3-(isobutoxy-3-nitrobenzoyl)aminopyridine Sodium hydrogen carbonate (350 mg, 4.17 mmol) was added to a solution of 2,3-diaminopyridine (228 mg, 2.09 mmol) in water (2 mL) under cooling with ice. To the solution was further added a solution of 4-isobutoxy-35 nitrobenzoyl chloride (108 mg, 2.09 mmol) in ethyl acetate (2 mL). The mixture was stirred for 2 hours under cooling with ice. The ethyl acetate was distilled off under reduced pressure, and to the residue was added water. The resulting solid product was collected by filtration, dried in air, subjected to silica gel column chromatography, and eluted using chloroform/methanol (30/1). There was produced 54 mg (yield 41%) of the desired compound in the form of a yellow powdery product.

$^1$H NMR (DMSO-d$_6$, 400 MHz) δ: 1.00 (6H, d, J=7 Hz), 2.0-2.1 (1H, m), 4.04 (2H, d, J=6 Hz), 5.83 (2H, s), 6.60 (1H, dd, J=5 Hz, 7 Hz), 7.48 (1H, J=9 Hz), 7.50 (1H, d, J=5 Hz), 7.81 (1H, broad d, J=5 Hz), 8.25 (1H, broad d, J=9 Hz), 8.52 (1H, broad s), 9.72 (1H, s).

(2) 2-(4-isobutoxy-3-nitrophenyl)imidazolo[4,5-b]-pyridine

A mixture of 2-amino-3-(4-isobutoxy-3-nitrobenzoyl)-aminopyridine (40 mg) and phosphorus oxychloride (2 mL) was heated to 120° C. for 8 hours under stirring. Excessive phosphorus oxychloride was distilled off under reduced pressure, and ice water was added to the residue. The precipitated solid product was collected by filtration, washed with water, and dried successively in air and at 60° C. under reduced pressure, to give 42 mg (yield 100%) of the desired compound in the form of a white powdery product.

$^1$H NMR (DMSO-$d_6$, 400 MHz)δ: 1.01 (6H, d, J=7 Hz), 2.1-2.2 (1H, m), 4.06 (2H, d, J=6 Hz), 7.3-7.35 (1H, m), 7.60 (1H, d, J=9 Hz), 8.10 (1H, broad s), 8.40 (1H, broad s), 8.48 (1H, dd, J=2 Hz, 9 Hz), 8.73 (1H, d, J=2 Hz).

EXAMPLE 5

4-Hydroxy-2-(4-isobutyloxy-3-nitrophenyl)1,3-benzoxazole

(1) 2-Aminoresorcinol

2-Nitroresorcinol (1.00 g, 6.45 mmol) was dissolved in ethanol (10 mL). The solution was then stirred for 6 hours at room temperature in the presence of 10% Pd/C (340 mg, 0.32 mmol) under hydrogen gas atmosphere. Insolubles were removed by filtration, and the solvent was distilled off under reduced pressure, to give 779 mg (yield 97%) of the desired compound in the form of a brown crystalline product.

M.P.: 153-155° C. (decomp.) $^1$H NMR (CD$_3$OD/ CDCl$_3$=1/20, 400 MHz) δ: 6.37 (2H, d, J=8 Hz), 6.54 (1H, t, J=8 Hz).

(2) 4-Hydroxy-2-(4-isobutyloxy-3-nitrophenyl)-1,3benzoxazole

4-Isobutyloxy-3-nitrobenzoic acid (480 mg, 2.01 mmol) and 2-aminoresorcinol (250 mg, 2.00 mmol) were suspended in dry dichloromethane (12 mL). 1-ethyl-3-(3'-dimethylaminopropyl)carbodiimide hydrochloride (WSC•HCl) (420 mg, 2.19 mmol), dry THF (6 mL) and dry DMF (6 mL) were added to the suspension. The mixture was then stirred for 19 hours at room temperature. Water (40 mL) and chloroform (20 mL) were added, and the organic portion was separated. The organic portion was then washed successively with water (20 mL×2) and aqueous saturated brine (20 mL), dried over anhydrous sodium sulfate, and placed under reduced pressure to distill the solvent off.

The residue was purified by silica gel column chromatography (methanol/chloroform=1/100) and subsequently crystallized from chloroform/hexane (1/3, 1.6 mL), to give 97 mg (yield 14%) of N-(2,6-dihydroxyphenyl.)-4-isobutyloxy3-nitrobenzamide in the form of a brown crystalline product.

Forty mg (0.12 mmol) of the above-obtained product was heated to 225-227° C. for one hour and purified by silica gel column chromatography (ethyl acetate/hexane=1/2), to give 13.6 mg (yield 36%) of the desired compound in the form of a pale yellow crystalline product.

$^1$H NMR (DMSO-$d_6$, 400 MHz) δ: 1.05 (6H, d, J=6 Hz), 2.0-2.2 (1H, m), 4.07 (2H, d, J=7 Hz), 6.79 (1H, dd, J=1 Hz, 7 Hz), 7.1-7.3 (2H, m), 7.59 (1H, d, J=9 Hz), 8.37 (1H, dd, J=2 Hz, 9 Hz), 8.58 (1H, d, J=2 Hz). IR (KBr) cm$^{-1}$: 2962, 2933, 1624, 1527, 1506, 1489, 1470, 1350, 1273, 1244, 1169, 1007. FAB-MS (m/e): 329 (M+1).

EXAMPLE 6

6-Amino-8-(4-isobutoxy-3-nitrophenyl)purine (1) 4,6-Diamino-5-(4-isobutoxy-3-nitrobenzoyl)aminopyridine A solution of 4-isobutoxy-3-nitrobenzoyl chloride (538 mg, 2.09 mmol) in 1,4-dioxane (2 mL) was dropwise added to a suspension of 4,5,6-triaminopyrimidine sulfate (466 mg, 2.09 mmol) in aqueous 1M sodium hydroxide (4.18 30 mL) under cooling with ice. The resulting mixture was stirred for 4 hours at the same temperature. Water (12 mL) was added to the reaction mixture. The precipitated solid product was collected by filtration, dried in air, and subjected to silica gel column chromatography. The elute using chloroform/methanol (10/1) gave 144 mg (yield 20%) of the desired compound in the form of a yellow powdery product.

$^1$H NMR (DMSO-$d_6$, 400 MHz) δ: 1.00 (6H, d, J=7 Hz), 2.0-2.1 (1H, m), 4.03 (2H, d, J=7 Hz), 5.99 (4H, s), 7.45 10 (1H, d, J=9 Hz), 7.76 (1H, s), 8.23 (1H, dd, J=2 Hz, 9 Hz), 8.49 (1H, d, J=2 Hz), 9.26 (1H, s).

(2) 6-Amino-8-(4-isobutoxy-3-nitrophenyl)purine

A mixture of 4,6-diamino-5-(4-isobutoxy-3-nitrobenzoyl) aminopyridine (40 mg, 0.115 mmol) and phosphorus oxychloride (2 mL) was heated to 120° C. for 8 hours under stirring. Excessive phosphorus oxychloride was distilled off under reduced pressure. Ice-water was added to the residue. The precipitated solid product was collected by filtration, washed with water, and dried in air. Methanol (1.5 mL) was added to the dried product was added methanol (1.5 mL), and the mixture was stirred for 2 hours at room temperature.

The precipitated solid product was collected by filtration and dried in air, to give 20 mg (yield 74%) of the desired compound in the form of a yellow powder product.

1H NMR (DMSO-$d_6$, 400 MHz) δ: 1.00 (6H, d, J=6 Hz), 2.0-2.1 (1H, m), 4.08 (2H, d, J=6 Hz), 7.63 (1H, d, J=9 Hz), 8.38 (1H, dd, J=2 Hz, 9 Hz), 8.58 (1H, s), 8.64 (1H, d, J=2 Hz).

EXAMPLE 7

4-Hydroxy-2-(4-isobutoxy-3-nitrophenyl)-1H-benzimidazole 2,3-diaminophenol (1.86 g, 15.0 mmol) was suspended in dry THF (150 mL). A solution of 4-isobutoxy-3-nitrobenzoyl chloride (2.50 mmol) in THF (10 mL) for a period of more than 30 minutes was dropwise added to the suspension. The resulting mixture was stirred for 3.5 hours under cooling with ice. The solvent was distilled off under reduced pressure. The residue was suspended in water (150 mL) and stirred for one hour at room temperature. The crystalline product was collected by filtration, washed with water (20 mL×5), and dried at room temperature under reduced pressure. The obtained crude product was purified by silica gel column chromatography (methanol/chloroform=1/25), to give 250 mg (yield 29%) of an amide compound in the form of a brown crystalline product.

The obtained amide product (225 mg) was heated to 185° C. for 15 min. The heated product was allowed to stand to room temperature. The obtained crude product was purified by silica gel column chromatography (ethyl acetate/hexane=1/1), to give 83 mg (yield 39%) of the desired compound in the form of a brown crystalline product.

M.p.: 244-249° C. (decomp.) $^1$H NMR (DMSO-d$_6$, 400 MHz) δ: 1.01 (6H, d, J=6 Hz), 2.0-2.2 (1H, m), 4.03 (2H, d, J=6 Hz), 6.58 (1H, bs), 6.9-7.1 (2H, m), 7.54 (1H, d, J=9 Hz), 8.42 (1H, bs), 8.69 (1H, bs), 9.76 (1H, bs), 12.86 (1H, bs).

EXAMPLE 8

2-(4-Isobutoxy-3-nitrophenyl)benzoxazole-7carboxylic acid (1) Methyl 3-aminosalicylate 3-Aminosalicylic acid (690 mg, 4.51 mmol), methanol 5 (45 mL), and conc. sulfuric acid (0.9 mL) were mixed, and heated for 55 hours under reflux. The methanol was distilled off under reduced pressure. To the residue was added cooled water. The aqueous residue was made alkaline by addition of aqueous saturated sodium hydrogen carbonate under cooling with ice. Thus precipitated crystalline product were collected by filtration, washed with two portions of water, and dried in vacuo at 40° C. for 40 min., to give 710 mg of a pale pink crystalline product. The product was suspended in chloroform (35 mL), and insolubles were removed by filtration. The filtrate was dried over sodium sulfate and then concentrated under reduced pressure to give 181 mg (yield 25.9%) of the desired compound in the form of a brown crystalline product. $^1$H NMR (CDCl$_3$, 400 MHz) δ: 3.88 (2H: broad s), 3.94 (3H, s), 6.71 (1H, dd, J=8 Hz, 8 Hz), 6.87 (1H, d, J=8 Hz), 7.24 (1H, m), 10.88 (1H, s).

(2) Methyl 3-(4-isobutoxy-3-nitrobenzoylamino)salicylate 4-Isobutoxy-3-nitrobenzoic acid (259 mg, 1.08 mmol) and methyl 3-aminosalicylate (181 mg, 1.08 mmol) were dissolved in dry dichloromethane (25 mL). WSC•HCl (207 mg, 1.08 mmol) was added to the resulting solution. The mixture was then stirred for 14 hours at room temperature. The solvent was distilled off at room temperature under reduced pressure. Water was added to the residue and the aqueous residue was subjected to extraction with, ethyl acetate. The ethyl acetate portion was successively washed with 2M hydrochloric acid, water, aqueous saturated sodium hydrogen carbonate, and aqueous saturated brine, and dried over sodium sulfate. The solvent-was distilled off under reduced pressure, to give 320 mg of a brown oil. The obtained oil was subjected to silica gel column chromatography. The oil was washed from the column with ethyl acetate/hexane (1/4) and then eluted using ethyl acetate/hexane (1/2), to give 115 mg (yield 27.4%) of the desired compound in the form of a. white crystalline product.

M.P.: 142-1440C $^1$H NMR (CDCl$_3$, 400 MHz)δ: 1.08 (6H, d, J=7 Hz), 2.115 2.3 (1H, m), 3.95 (2H, d, J=6 Hz), 3.99 (3H, s), 6.96 (1H, dd, J=8 Hz, 8 Hz), 7.16 (1H, d, J=9 Hz), 7.61 (1H, dd, J=2 Hz, 8 Hz), 8.09 (1H, dd, J=2 Hz, 9 Hz), 8.40 (1H, d, J=2 Hz), 8.51 (1H, broad s), 8.67 (1H, dd, J=2 Hz, 8 Hz), 11.40 (1H, s). IR (KBr, cm 1): 3320, 1700, 1645, 1.620, 1545, 1530, 1435, 1340, 1270.

(3) Methyl 2-(4-isobutoxy-3-nitrophenyl)benzoxazole-7carboxylate

Methyl 3-(4-isobutoxy-3-nitrobenzoylamino)salicylate (115 mg, 0.3 mmol) and phosphorus oxychloride (1.1 mL) were mixed and stirred at 110° C. for 4 hours. The stirred mixture was then cooled to room temperature, poured onto ice blocks, and extracted with ethyl acetate. The ethyl acetate portion was successively washed with water, aqueous saturated water, and aqueous saturated brine, and dried over sodium sulfate. The solvent was distilled off under reduced pressure, to give 97 mg of a pale yellow crystalline product. The obtained product was recrystallized from ethyl acetate (2 mL), to give 40 mg of the desired compound in the form of a white crystalline product. The mother liquor was concentrated, and the residue was recrystallized from ethyl acetate-hexane, to give 42 mg of the desired compound in the form of a white crystalline product. Total 82 mg (yield 73%)

M.P.: 128-1290C $^1$H NMR (CDCl$_3$) δ: 1.09 (6H, d, J=7 Hz), 2.1-2.3 (1H, m), 3.98 (2H, d, J=6 Hz), 4.07 (3H, s), 7.22 (1H, d, J=9 Hz), 7.44 (1H, dd, J=8 Hz, 8 Hz), 7.95 (1H, d, J=2 Hz). 8 Hz), 8.01 (1H, dd, J=1 Hz, 8 Hz), 8.45 (1.H, dd, J=2 Hz, 15 9 Hz), 8.75 (1H, d, J=2 Hz). IR (KBr, cm 1): 1720, 1625, 1520, 1345, 1315, 1300, 1285.

(4) 2-(4-Isobutoxy-3-nitrophenyl)benzox:azole-7-carboxyl.ic acid

Methyl 2-(4-isobutoxy-3-nitrophenyl)benzoxazole-7carboxylate (22 mg, 0.06 mmol) was suspended in methanol (1.8 mL). Tetrahydrofuran (2.4 mL) and 1M NaOH (0.6 mL) were successively added to the suspension, and the mixture was stirred at 50° C. for 2 hours. A small amount of insoluble was removed by filtration, and the filtrate was concentrated under reduced pressure. The residue was suspended in water, made acidic by addition of 2M hydrochloric acid (0.6 mL), and extracted with ethyl acetate. The ethyl acetate portion was washed successively with water and aqueous saturated brine, and dried over sodium sulfate. The solvent was distilled off under reduced pressure, to give 21 mg of a pale yellow crystalline product. The obtained product was recrystallized from ethyl acetate hexane (4 mL-8 mL), to give 15 mg (yield 70%) of the desired compound in the form of a pale yellow crystalline product.

M. P.: 258-2600C $^1$H NMR (CDCl3)δ: 1.10 (6H, d, J=7 Hz), 2.1-2.3 (1H, m), 3.99 (2H, J=6 Hz), 7.25 (1H, d, J=:9 Hz), 7.48 (1H, 10 dd, J=8 Hz, 8 Hz), 8.01 (1H, dd, J=1 Hz, 8 Hz), 8.07 (1H, dd, J=1 Hz, 8 Hz), 8.47 (1H, dd, J=2 Hz, 9 Hz), 8.78 (1H, d, J=2 Hz).

EXAMPLE 9

2-(4-Isobutoxy-3-nitrophenyl)-3H-imidazo[4,5-c]pyridine

4-Isobutoxy-3-nitrobenzoic acid (240 mg, 1.00 mmol) and 3,4-diaminopyridine (153 mg, 1.40 mmol) were dissolved in dry DMF (10 mL). To the solution was added DCC (227 mg, 1.10 mmol) under cooling with ice. The solution was then stirred for 3 days at room temperature. Icewater (30 mL) was added, and the precipitated crystalline product was filtered, and washed with water (3 mL×3). The obtained residue was purified by silica gel column chromatography (methanol/chloroform=1/15), to give 13 mg (yield 4%) of an amide compound in the form of a pale brown crystalline product.

Subsequently, 8 mg (0.024 mmol) of the amide product; was heated to 190° C. for 15 min, and allowed to stand to room temperature. The obtained crude product was subjected to thin layer chromatography (methanol/chloroform=1/10), to give 5 mg (yield 66%) of the desired compound in the form of a yellow crystalline product.

$^1$H NMR (CDCl$_3$/CD$_3$OD=20/1, 400 MHz) δ: 1.09 (6H, d, J=7 Hz), 2.1-2.3 (1H, m), 3.97 (2H, d, J=7 Hz), 7.25 (1H, 5 d, J=9 Hz), 7.64 (1H, d, J=6 Hz), 8.30 (1H, d, J=6 Hz), 8.44 (1H, dd, J=2 Hz, 9 Hz), 8.66 (1H, d, J=2 Hz), 8.93 (1H, s).

EXAMPLE 10

2-(3-Cyano-4-isobutyloxyphenyl)-1,3-benzothiazole-7-carboxylic acid (1) Ethyl 3-Cyano-4-isobutylbenzoate Ethyl 4-nitrobenzoate (50.0 g, 256 mmol) and potassium cyanide (51.2 g, 786 mmol) were added to DMSO (380 mL), stirred at 100° C. for 4 hours, and cooled to room temperature. DMSO was distilled off, and to the residue was added ice-water (200 mL). The aqueous residue was washed with ethyl acetate (100 mL). To the mixture was added conc. hydrochloric acid, to change the pH of the mixture to 1. The mixture was then extracted with ethyl acetate (200 mL), washed with aqueous saturated brine (50 mL), dried over anhydrous sodium sulfate, and placed under reduced pressure to distill the solvent off. There was obtained 51.4 g of ethyl 3-cyano-4-hydroxybenzoate as a crude product.

Isobutyl bromide (56.1 mL, 512 mmol) was added to a suspension of the ethyl 3-cyano-4-hydroxybenzoate crude product (51.4 g) and potassium carbonate (70.8 g, 512 mmol) in dry DMF (200 mL), stirred at 100° C. for 10 hours, and cooled to room temperature. Ice-water (500 mL) was then added to the cooled suspension. The aqueous mixture was extracted with ethyl acetate (200 mL×2). The ethyl acetate portion was washed successively with water (500 mL×2) and aqueous saturated brine (200 mL), dried over anhydrous sodium sulfate, and placed under reduced pressure to distill the solvent off. The residue was purified by silica gel column chromatography (ethyl acetate/hexane=1/4). The resulting crystalline product was dissolved in ethyl acetate (50 mL) under heating. The mixture was kept hot, while hexane (100 mL) was added to the mixture. The hexane solution was stirred and cooled to room temperature, and further stirred for 10 min. under cooling with ice. The precipitated crystalline product was collected by filtration, washed successively with ethyl acetate/hexane (1/5, 60 mL) mixture and hexane (500 mL), and dried in air, to give 20.8 g (yield 33%) of the desired compound in the form of a pale yellow crystalline product.

M.P.: 105.6-106.40C $^1$H NMR (CDCl$_3$, 400 MHz)δ: 1.09 (6H, d, J=7 Hz), 1.39 (3H, t, J=7 Hz), 2.1-2.3 (1H, m), 3.90 (2H, d, J=7 Hz), 4.37 (2H, q, J=7 Hz), 6.98 (1H, d, J=9 Hz), 8.19 (1H, dd, J=2 Hz, 9 Hz), 8.25 (1H, d, J=2 Hz).

(2) 3-Cyano-4-isobutylbenzoic acid

Ethyl 3-cyano-4-isobutyloxybenzoate (20.0 g, 80.9 mmol) was dissolved in a mixture of ethanol (100 mL) and THF (100 mL). Aqueous 2M sodium hydroxide (45 mL, 90.0 mmol) was added to the resulting solution, and the mixture was stirred at 30° C. for 4 hours. The solvent was distilled off under reduced pressure. Water (100 mL) was added to the residue and further aqueous 2M hydrochloric acid to obtain an aqueous mixture of pH 1. The precipitated crystalline product was collected by filtration, washed with water (200 mL×2), and dried in air, to give 17.5 g (yield 99%) of the desired compound in the form of a white crystalline product.

M.P.: 220.4-221.60C $^1$H NMR (CDCl$_3$, 400 MHz)δ: 1.09 (6H, d, J=6 Hz), 2.12.3 (1H, m), 3.91 (2H, d, J=6 Hz), 7.00 (1H, d, J=9 Hz), 8.21 (1H, dd, J=2 Hz, 9 Hz), 8.27 (1H, d, J=2 Hz).

(3) Methyl 3-amino-2-chlorobenzoate

A mixture of 3-amino-2-chlorobenzoic acid (500 mg, 2.91 mmol), conc. sulfuric acid (6 mL), and methanol (150 mL) was heated under reflux for 24 hours, and placed under reduced pressure to distill the solvent off. The residue was neutralized by addition of aqueous saturated sodium hydrogen carbonate. The neutralized mixture was extracted with toluene, dried over anhydrous magnesium sulfate, and placed under reduced pressure to distill the solvent off. There was obtained 497 mg (yield 92%) of the desired compound in the form of pale brown oil.

$^1$H NMR (CDCl$_3$, 500 MHz)δ: 3.91 (3H, s), 4.23 (2H, broad s), 6.89 (1H, dd, J=1 Hz, 8 Hz), 7.10 (1H, dd, J=8 Hz, 8 Hz), 7.16 (1H, dd, J=1 Hz, 8 Hz).

(4) Methyl 2-chloro-3-(3-cyano-4-isobutyloxybenzoylamino)benzoate

Oxalyl chloride (889 mg, 7.0 mmol) was dropwise added to a solution of 3-cyano-4-isobutyloxybenzoic acid (767 mg, 3.5 mmol) in dichloromethane (10 mL) under cooling with ice. Subsequently, a catalytic amount of DMF was added. The mixture was then stirred for one hour at room temperature, heated under reflux for 3 hours, and placed under reduced pressure to distill the solvent off. Toluene was added to the residue and the solvent was distilled off under reduced pressure. THF (10 mL) was added to the residue. Further, a solution of methyl 3 amino-2-chlorobenzoate (497 mg, 2.68 mmol) and triethylamine (1.39 mL, 10 mmol) in THF (10 mL). The resulting mixture was stirred for 14 hours at room temperature, and toluene and aqueous 1M hydrochloric acid were added. The organic portion was taken out, washed with aqueous 1M hydrochloric acid and aqueous saturated sodium hydrogen carbonate, dried over anhydrous magnesium sulfate, and placed under reduced pressure to distill the solvent off.

The residue was purified by silica gel column chromatography (ethyl acetate/toluene=1/20), to give 900 mg (purity 82%, yield 71%) of the desired compound as an oil.

$^1$H NMR (CDCl$_3$, 500 MHz) δ: 1.06 (6H, d, J=6 Hz), 2.12.4 (1H, m), 3.87 (2H, d, J=6 Hz), 3.95 (3H, s), 6.93 (1H, d, J=9 Hz), 7.1-7.3 (2H, m), 7.83 (1H, dd, J=2 Hz, 8 Hz), 7.89 (1H, dd, J=2 Hz, 9 Hz), 7.98 (1H, d, J=2 Hz).

(5) Methyl 2-chloro-3-(3-cyano-4-isobutyloxybenzoylamino)benzoate

A solution of methyl 2-chloro-3-(3-cyano-4-isobutyl-oxybenzoylamino)benzoate (1.07 g, purity 82%, 2.27 mmol) and Lawesson's reagent (1.23 g, 2.77 mmol) in toluene (20 mL) was heated under reflux for 5 hours, and placed under reduced pressure to distill the solvent off. The residue was purified by silica gel column chromatography (ethyl acetate/toluene=1/40), to give 670 mg (yield 73%) of the desired compound as an oil.

$^1$H NMR (CDCl$_3$, 500 MHz) δ: 1.09 (6H, d, J=7 Hz), 2.2-2.3 (1H, m), 3.92 (2H, d, J=7 Hz), 3.96 (3H, s), 7.01 (1H, d, J=9 Hz), 7.1-7.3 (1H, m), 7.43 (1H, dd, J=8 Hz, 8 Hz), 7.78 (1H, dd, J=1 Hz, 8 Hz), 8.10 (1H, d, J=9 Hz), 8.15 (1H, 5 d, J=1 Hz).

(6) Methyl 2-(3-cyano-4-isobutyloxyphenyl)-1,3-benzothiazole-7-carboxylate

A solution of methyl 2-chloro-3-(3-cyano-4-isobutyloxybenzoylamino)benzoate (670 mg, 1.66 mmol) in THF (5 mL) was dropwise added to a suspension of sodium hydride (200 mg, 4.98 mmol) in THF (5 mL) under cooling with ice. The mixture was stirred for 2 hours at room temperature, poured into ice-water, and extracted with toluene. The toluene portion was dried over anhydrous magnesium sulfate, and placed under reduced pressure to distill the solvent off. The residual crystalline product was recrystallized from hexane, to give 288 mg (yield 47%) of the desired compound in the form of a crystalline product.

$^1$H NMR (CDCl$_3$, 500 MHz) δ: 1.11 (6H, d, J=6 Hz), 2.1-2.3 (1H, m), 3.93 (2H, d, J=6 Hz), 4.05 (3H, s), 7.08 (1H, d, J=9 Hz), 7.59 (1H, dd, J=8 Hz, 8 Hz), 8.13 (1H, dd, J=2 Hz, 8 Hz), 8.24 (1H, dd, J=2 Hz, 8 Hz), 8.27 (1H, dd, J=2 Hz, 9 Hz), 8.39 (1H, d, J=2 Hz).

(7) 2-(3-Cyano-4-isobutyloxyphenyl)-1,3-benzothiazole-7-carboxylic acid

Methyl 2-(3-cyano-4-isobutyloxyphenyl)-1,3-benzothiazole-carboxylate (288 mg, 0.786 mmol) was dissolved in a mixed solvent (50 mL) of methanol/ethanol/THF (2/1/2), and, then a solution of potassium hydroxide (281 mg, 5 mmol) in water (10 mL) was added and stirred for one hour at room temperature. The mixture was made acidic by addition of aqueous 1M hydrochloric acid, and placed under reduced pressure to distill the solvent off. The residue was extracted with chloroform. The chloroform portion was then dried over anhydrous magnesium sulfate and placed under reduced pressure too distill the solvent off. The residual crystalline product was recrystallized from toluene, to give 230 mg (yield 83%) of the desired compound in the form of a white crystalline product.

M.p.: 268-270° C. $^1$H NMR (DMSO-d$_6$, 400 MHz) δ: 1.04 (6H, d, J=7 Hz), 2.0-2.2 (1H, m), 4.05 (2H, d, J=7 Hz), 7.44 (1H, d, J=9 Hz), 7.69 (1H, dd, J=8 Hz, 8 Hz), 8.10 (1H, dd, J=1 Hz, 8 Hz), 8.30 (1H, dd, J=1 Hz, 8 Hz), 8.41 (1.H, dd, J=2 Hz, 9 Hz), 8.47 (1H, d, J=2 Hz). IR (KBr, cm−1): 2966, 2875, 1608, 1518, 1477, 1471, 1396, 1306, 1282, 1240, 1238, 1211, 1155, 1009.

EXAMPLE 11

2-(3-Cyano-4-isobutyloxyphenyl)benzimidazole-7-carboxylic acid

(1) 3-Nitrophthalamine

3-Nitrobenzoic anhydride (9.65 g, 50 mmol) was divided into three portions and added by portions to aqueous ammonia (28%) under cooling with ice. The mixture was stirred at 60° C. for 12 hours, and placed under reduced pressure to distill the solvent off. The residue was made acidic by addition of aqueous 12M hydrochloric acid. The precipitated crystalline product was collected by filtration, washed with water, and dried in air, to give 9.86 g (yield 94%) of the desired compound in the form of a white crystalline product.

$^1$H NMR (DMSO-d$_6$, 400 MHz) δ: 7.65 (1H, broad s), 7.78 5 (1H, dd, J=8 Hz, 8 Hz), 8.06 (1H, broad s), 8.18 (1H, dd, J=1 Hz, 8 Hz), 8.24 (1H, dd, J=1 Hz, 8 Hz).

(2) 3-Nitroanthranilic acid

Bromine (2.56 mL, 48 mmol) was dropwise added to an aqueous potassium hydroxide solution (24.1 g, 430 mmol in 110 mL) under cooling with ice. The resulting solution was added to 3-nitrophthalamine (9.86 g, 47 mmol), and the mixture was stirred at 60° C. for 3 hours, and then stirred for 12 hours at room temperature. The precipitated orange crystalline product was collected by filtration, dissolved in water (50 mL), and made acidic by addition of aqueous 6M hydrochloric acid. The precipitated crystalline product was collected by filtration, washed with several portions of water, and dried in air, to give 6.0 g (yield 70%) of the desired compound in the form of a yellow crystalline product.

(3) Methyl 3-nitroanthranilate

Thionyl chloride (14.6 mL, 200 mmol) was dropwise added to methanol (150 mL) under cooling with ice. The resulting solution was added 3-nitroanthranilic acid (3.65 g, 20 mmol), heated under reflux for 23 hours, and then placed under reduced pressure to distill the solvent off. To the residue were added toluene and aqueous saturated sodium hydrogen carbonate. The organic portion was taken out, dried over anhydrous magnesium sulfate, and placed under reduced pressure to distill the solvent off.

There was obtained 2.68 g (yield 68) of the desired compound in the form of a yellow crystalline product.

$^1$H NMR (CDCl$_3$, 500 MHz) δ: 3.92 (3H, s), 6.66 (1H, dd, J=8 Hz, 8 Hz), 8.24 (1H, dd, J=2 Hz, 8 Hz), 8.38 (1H, dd, 5 J=2 Hz, 8 Hz).

(4) Methyl 3-aminoanthranilate

To a solution of methyl 3-nitroanthranilate (1.44 g, 7.34 mmol) in methanol (50 mL) was added 10% Pd/C (300 mg), and the resulting mixture was stirred for 12 hours at room temperature under hydrogen atmosphere. The 10% Pd/C was removed, and the solvent was distilled off under reduced pressure, to give 1.22 (quantitative yield) of the desired compound in the form of a brown crystalline product.

(5) Methyl 3-(3-cyano-4-isobutyloxybenzoylamino)anthranilate

Thionyl chloride (3.06 mL, 42 mmol) and a catalytic amount of DMF were successively added to a solution of 3cyano-4-isobutyloxybenzoic acid (1.53 g, 7.0 mmol) in dichloromethane (15 mL). The mixture was heated under reflux for 4 hours, and placed under reduced pressure to distill the solvent off. To the residue was added THF (20 mL) under cooling with ice. The residue solution was then dropwise added to a solution of methyl 3-amino anthranilate (1.22 g, 7.34 mmol) and triethylamine (2 mL) in THF (20 mL), and the mixture was stirred at 45° C. for 5 hours. The precipitated crystalline product was collected by filtration and washed with several portions of ethyl acetate, to give 2.11 g (yield 82%) of the desired compound in the form of a pale green crystalline product.

$^1$H NMR (DMSO-d$_6$, 500 MHz) δ: 1.03 (6H, d, J=7 Hz), 2.0-2.2 (1H, m), 3.82 (3H, s), 4.02 (2H, d, J=7 Hz), 6.56.7 (3H, m), 7.35 (1H, dd, J=2 Hz, 8 Hz), 7.39 (1H, d, J=9 Hz), 7.72 (1H, dd, J=2 Hz, 8 Hz), 8.25 (1H, dd, J=2 Hz, 5 9 Hz), 8.41 (1H, d, J=2 Hz), 9.74 (1H, S).

(6) 2-(3-Cyano-4-isobutyloxyphenyl)benzimidazole-7-carboxylic acid

A solution of methyl 3-(3-cyano-4-isobutyloxybenzoylamino)anthranilate (341 mg, 0.93 mmol) in glacial acetic acid (10 mL) was heated under reflux for 2 hours, cooled, and placed under reduced pressure to distill the solvent off. To the residue was added a solution of sodium hydroxide (240 mg, 10 mmol) in methanol (20 mL), and the mixture was stirred for 5 hours at room temperature. The reaction mixture was made acidic by addition of aqueous 1M hydrochloric acid, and placed under reduced pressure to distill the solvent off. To the residue were added ethyl acetate and water. The organic portion was taken out, dried over anhydrous magnesium sulfate, and placed under reduced pressure to distill the solvent off. The residue was washed with hot toluene, to give 300 mg (yield 960) of the desired compound in the form of a pale yellow crystalline product.

M.p.: 299-302° C. $^1$H NMR (DMSO-$d_6$, 400 MHz) δ: 1.04 (6H, d, J=7 Hz), 2.0-2.2 (1H, m), 4.03 (2H, d, J=7 Hz), 7.32 (1H, dd, J=8 Hz, 8 Hz), 7.42 (1H, d, J=9 Hz), 7.82 (1H, d, J=8 Hz), 7.91 (1H, d, J=8 Hz), 8.58 (1H, dd, J=2 Hz, 9 Hz), 8.79 (1H, broad s), 12.46 (1H, broad s), 13.48 (1H, broad s). IR (KBr, cm−1): 3319, 1500, 1498, 1433, 1302, 1281, 1238, 1209, 1147, 762.

EXAMPLE 12

2-(3-Cyano-4-isobutyloxyphenyl)-7-hydroxy 1,3-benzothiazole (1)
3-Cyano-4-isobutyloxy-N-(3-methoxyphenyl)benzamide Dichloromethane (20 mL) was added to a mixture of 3cyano-4-isobutyloxybenzoic acid (2.19 g, 10 mmol), m-anisidine (1.85 g, 15 mmol), 1-[3-(dimethylamino)propyl]3-ethylcarbodiimide hydrochloride (WSC•HCl, 3.83 g, 20 mmol), and 4-(dimethylamino)pyridine (244 mg, 2.0 mmol). The resulting mixture was then stirred for 21 hours at room temperature. To the mixture was added aqueous 1M hydrochloric acid (30 mL), and the resulting mixture was extracted with ethyl acetate (40 mL). The ethyl acetate portion was washed with aqueous saturated sodium hydrogen carbonate, dried over anhydrous magnesium sulfate, and placed under reduced pressure to distill the solvent off. The residue was recrystallized from toluene, to give 2.87 g (yield 89%) of the desired compound in the form of a crystalline product.

$^1$H NMR (CDCl$_3$, 500 MHz) δ: 1.09 (6H, d, J=6 Hz), 2.12.3 (1H, m), 3.83 (3H, s), 3.90 (2H, d, J=6 Hz), 6.72 (1H, dd, J=1 Hz, 8 Hz), 7.03 (1H, d, J=8 Hz), 7.12 (1H, dd, J=1 Hz, 8 Hz), 7.2-7.3 (1H, m), 7.40 (1H, dd, J=2 Hz, 2 Hz), 7.92 (1H, broad s), 8.0-8.2 (1H, m).

(2) 3-Cyano-4-isobutyloxy-N-(3-methoxyphenyl) thiobenzamide

A solution of 3-cyano-4-isobutyloxy-N-(3-methoxyphenyl)benzamide (972 mg, 3.0 mmol) and Lawesson's reagent (808 mg, 2.0 mmol) in toluene (5 mL) was heated under reflux for 3.5 hours. After addition of toluene (approx. 20 mL), the heated solution was allowed overnight to lapse at room temperature. The precipitated crystalline product was collected by filtration, to give 900 mg (yield 88%) of the desired compound in the form of a yellow crystalline product.

$^1$H NMR (CDCl$_3$, 500 MHz) δ: 1.08 (6H, d, J=7 Hz), 2.12.3 (1H, m), 3.83 (3H, s), 3.89 (2H, d, J=7 Hz), 6.8-7.0 (2H, m), 7.0-7.8 (2H, m), 7.8-8.2 (2H, m), 8.8-8.6 (1H, m).

(3) 2-(3-Cyano-4-isobutyloxyphenyl)-7-methoxy-1, 3-benzothiazole

Dioxane (70 mL) and water (70 mL) were added to a mixture of 3-cyano-4-isobutyloxy-N-(3-methoxyphenyl) thiobenzamide (900 mg, 2.64 mmol), potassium ferricyanide (2.61 g, 7.93 mmol), and potassium hydroxide (892 mg, 15.9 mmol). The resulting mixture was stirred for 20 hours at room temperature. The mixture was then placed under reduced pressure to distill the solvent off, and extracted with ethyl acetate (50 mL). The ethyl acetate portion was washed with water, dried over anhydrous magnesium sulfate, and placed under reduced pressure to distill the solvent off. The residue was purified by silica gel column chromatography (ethyl acetate/toluene=1/20-1/10), to give 322 mg (yield 36%) of the desired compound in the form of a pale yellow crystalline product.

$^1$H NMR (CDCl$_3$, 500 MHz) δ: 1.10 (6H, d, J=6 Hz), 2.12.3 (1H, m), 3.92 (2H, d, J=6 Hz), 4.02 (3H, s), 6.85 (1H, 30 d, J=8 Hz), 7.06 (1H, d, J=9 Hz), 7.45 (1H, dd, J=8 Hz, 8 Hz), 7.68 (1H, d, J=8 Hz), 8.23 (1H, dd, J=2 Hz, 9 Hz), 8.30 (1H, d, J=2 Hz).

(4) 2-(3-Cyano-4-isobutyloxyphenyl)-7-hydroxy-1, 3-benzothiazole

Ethane thiol (0.45 mL, 6.08 mmol) was added to lithium metal (14 mg, 2.02 mmol), and the mixture was stirred for one hour at room temperature. To tire mixture were then added dry DMF (5 mL) and 2-(3-cyano-4-isobutyloxyphenyl)-7-methoxy-1,3-benzothiazole (150 mg, 0.44 mmol). The resulting mixture was stirred at 80° C. for 8.5 hours, cooled to room temperature, and, after addition of icewater (10 mL), made to pH 7 by addition of aqueous 1M hydrochloric acid. The mixture was then extracted with ethyl acetate (20 mL). The ethyl acetate portion was washed successively with water (10 mL) and aqueous saturated brine (10 mL), dried over anhydrous sodium sulfate, and placed under reduced pressure to distill the solvent off. The residue was purified by silica, gel column chromatography (ethyl acetate/hexane=1/3), and suspended in hexane. The obtained crystalline product was collected by filtration, washed with hexane, and dried in air, to give 17 mg (yield 12%) of the desired compound in the form of a pale yellow crystalline product.

M.p.: 200-202° C. $^1$H NMR (DMSO-$d_6$, 400 MHz) δ: 1.04 (6H, d, J=6 Hz), 2.0-2.2 (1H, m), 4.03 (2H, d, J=6 Hz), 6.87 (1H, d, J=8 Hz), 7.36 (1H, dd, J=8 Hz, 8 Hz), 7.42 (1H, d, J=9 Hz), 7.51 (1H, d, J=8 Hz), 8.33 (1H, dd, J=2 Hz, 9 Hz), 8.38 (1H, d, J=2 Hz). IR (KBr, cm−:L): 3319, 2960, 2873, 2231, 1579, 1470, 1392, 1281, 1022, 787.

EXAMPLE 13

Pharmacological Experiment 1 (In Vitro Test)

1. Preparation of Test Sample

The test compound was dissolved in dimethylsulfoxide and diluted with 50 mM phosphate buffer (pH 7.5), to give a solution of a predetermined concentration.

2. Measurement 250 gL of each of the solutions of the test compound having different concentrations was added to 1 mL of a solution of Xanthine (SIGMA, 300 gM) in the 50 mM phosphor buffer (pH 7.5). The mixture was then pre-incubated at 37° C. for 10 min. Subsequently, to the pre-incubated mixture was added 250 mL of Cow milk Xanthine Oxidase (Roche) diluted with the 50 mM phosphate buffer (pH 7.5) to give a solution of 30 mU concentration. The mixture was then kept at 37° C. for 15 min for performing a reaction. The reaction was terminated by addition of 1N hydrochloric acid. Subsequently, the absorbance (OD 290 mm) was measured by means of a spectrophotometer (HITACHI U-2000), to obtain the inhibition ratio.

The inhibition ratio was calculated according to the following formula:

Inhibition ratio(%)=[1−(B−C)/(A−C)]×100

A: absorbance of control
B: absorbance measured in the case of using test compound
C: absorbance of blank 3. Test Results The test results are set forth in Table 20.

TABLE 20

| Example number | $IC_{50}$(nM) |
|---|---|
| Example 1-A | 63.2 |
| Example 1-B | 44.8 |
| Example 2 | 11.1 |
| Example 6 | 75.9 |
| Example 7 | 102.0 |
| Example 8 | 18.6 |
| Example 9 | 58.4 |
| Example 10 | 50.0 |
| Example 11 | 22.3 |
| Example 12 | 161.3 |
| Allopurinol | 542.1 |

As is apparent from Table 20, the compounds of the present invention show a xanthine oxidase inhibiting action superior to allopurinol.

EXAMPLE 14

Pharmacological Experiment 2 (In Vivo Test)

1. Test Animals, and Grouping

ICR mouse (Japan Charles River Co., Ltd., 6 W) was employed as test animal. One group comprised mice, and a vehicle control group was set for each experiment.

2. Preparation and Administration of the Test Compound

The test compound was suspended in aqueous 0.50 methylcellulose solution to for administration.

Dosage is 3 mg/10 mL/kg for each of the control groups and all test groups. The administration was made by single oral administration.

3. Procedure of Experiment

The test compound was orally administered once, and the whole blood was collected from main artery in the presence of heparin after one hour. From the collected whole blood was separated plasma in the conventional manner, and the plasma was subjected to measurement of uric acid value by the enzyme method by means of an automatic analytical apparatus (HITACHI 7060E).

The inhibition ratio was calculated according to the following formula:

Inhibition ratio(%)=(100−A/B)×100

A: average uric acid value in plasma of the group into which the test compound was administered.
B: average uric acid value in plasma of the vehicle control group 4. Test Results Test results are set forth in Table 21.

TABLE 21

| Example number | Inhibition ratio (%) |
|---|---|
| Example 1-B | 60.7 |
| Example 6 | 63.8 |
| Example 8 | 56.8 |
| Example 10 | 56.1 |
| Example 11 | 51.4 |

As is apparent from Table 21, the compounds of the present invention show a significant xanthine oxidase inhibiting action even in the experiment of in vivo.

What is claimed is:

1. Compounds of the following formula (I) or salts thereof

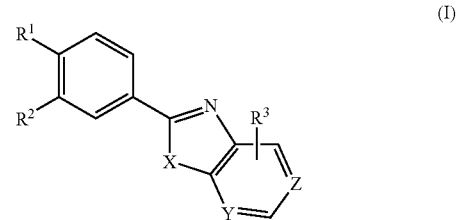

in which
R$^1$ represents an alkyl group having 1-8 carbon atoms, an alkyl group substituted with 1-3 halogen atoms, OR$^4$, CO$_2$R$^5$, or; S(O)$_n$R$^6$ wherein R$^4$ is hydrogen, or an alkyl group having 1-8 carbon atoms, an aralkyl group having an aryl moiety of 6-10 carbon atoms and an alkyl moiety of 1-4 carbon atoms, an alkylcarbonyl group having 2-9 carbon atoms, an arylcarbonyl group having an aryl moiety of 6-10 carbon atoms, an aralkylcarbonyl group having an aryl moiety of 6-10 carbon atoms and an alkylcarbonyl moiety of 2-5 carbon atoms or an aryl group having 6-10 carbon atoms which may have a substituent selected from the group consisting of halogen, hydroxyl, nitro and cyano; each of R$^5$ and R$^6$ is hydrogen or an alkyl group having 1-8 carbon atoms, an aralkyl group having an aryl moiety of 6-10 carbon atoms and an alkyl moiety of 1-4 carbon atoms, or an aryl group having 6-10 carbon atoms which may have a substituent selected from the group consisting of halogen, hydroxyl, nitro, cyano and amino; and n is an integer of 0 to 2;
R$^2$ is hydrogen, halogen, nitro, cyano, formyl, an alkyl group having 1-8 carbon atoms, an alkyl group having 1-8 carbon atoms which is substituted with one to three halogens, or CO$_2$R$^7$ wherein R$^7$ has the same meaning as R$^5$ above;
R$^3$ is hydrogen, halogen, hydroxyl, amino, CO$_2$R$^8$, PO(OH)(OR$^9$), S(O)$_m$R$^{10}$, or an alkyl group having 1-8 carbon atoms or an alkylaminocarbonyl group having alkyl of 1-8 carbon atoms which may have a substituent selected from the group consisting of halogen, hydroxyl, nitro, cyano and amino; wherein each of R$^8$, R$^9$, and R$^{10}$ has the same meaning as R$^5$ above; m has the same meaning as n above;
X is sulfur; and
each of Y and Z is nitrogen.

2. The compounds or salts of claim 1, wherein R$^1$ is OR$_4$.

3. The compounds or salts of claim 1, wherein $R^1$ is an alkoxy group having 1-5 carbon atoms.

4. The compounds or salts of claim 1, wherein $R^1$ is isobutoxy.

5. The compounds or salts of claim 1, wherein $R^2$ is nitro, cyano, halogen, or carboxyl.

6. The compounds or salts of claim 1, wherein $R^2$ is nitro or cyano.

7. The compounds or salts of claim 1, wherein $R^3$ is hydrogen, amino, hydroxyl, halogen, or carboxyl.

8. A xanthine oxidase inhibitor composition containing as an active ingredient, the compound or a salt of claim 1 and at least one compound selected from the group consisting of excipients, disintegrators, binders, lubricants, dyes, diluents, and combinations thereof.

9. A composition for treating hyperuricemia containing as an active ingredient, the compound or a salt of claim 1 and at least one compound selected from the group consisting of excipients, disintegrators, binders, lubricants, dyes, diluents and combinations thereof.

* * * * *